United States Patent [19]

Grabis

[11] 4,394,136

[45] Jul. 19, 1983

[54] SYSTEM FOR RECOVERING METHANE GAS FROM LIQUID WASTE

[75] Inventor: Dietrich W. Grabis, San Rafael, Calif.

[73] Assignee: United International California Corporation, San Rafael, Calif.

[21] Appl. No.: 336,884

[22] Filed: Jan. 4, 1982

[51] Int. Cl.³ .................................... C02F 11/04
[52] U.S. Cl. ............................ 48/111; 210/170; 405/53; 435/287; 435/801
[58] Field of Search ............ 48/111, 197 A; 435/167, 435/287, 316, 801; 210/170; 405/53, 55; 422/184

[56] References Cited

U.S. PATENT DOCUMENTS

| | | | |
|---|---|---|---|
| 4,050,907 | 9/1977 | Brimhall | 48/111 |
| 4,100,023 | 7/1978 | McDonald | 195/27 |
| 4,274,838 | 6/1981 | Dale et al. | 435/167 |
| 4,349,355 | 9/1982 | Lingappa et al. | 48/111 |

FOREIGN PATENT DOCUMENTS 2376209 7/1978 France ........................... 435/167

Primary Examiner—Peter F. Kratz
Attorney, Agent, or Firm—Flehr, Hohbach, Test, Albritton & Herbert

[57] ABSTRACT

A system for and method of recovering methane gas from liquid waste which is stored within a pit is disclosed herein. The methane gas is produced by causing the liquid waste to undergo anaerobic fermentation. Therefore, it is necessary to close the pit in an air tight fashion. This is carried out using a cover sheet which is fixedly disposed over the pit in an air tight but readily disengagable fashion. The liquid waste within this air tight pit is preferably agitated intermittently during its storage therein whereby to increase the amount of methane gas produced.

9 Claims, 7 Drawing Figures

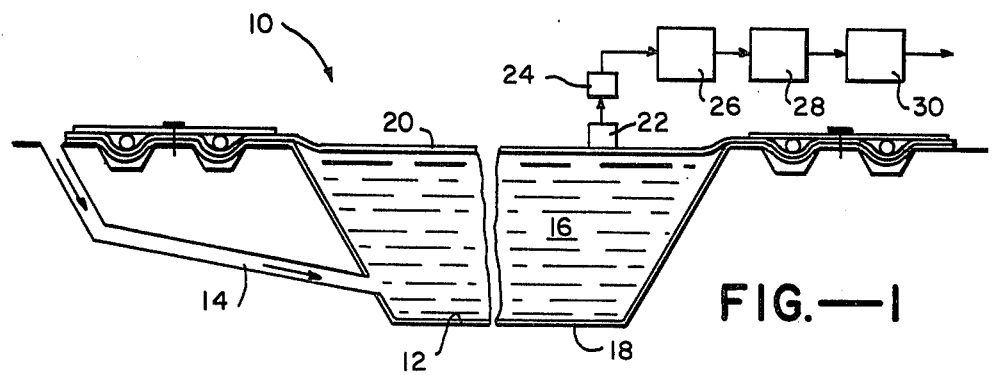
FIG.—1
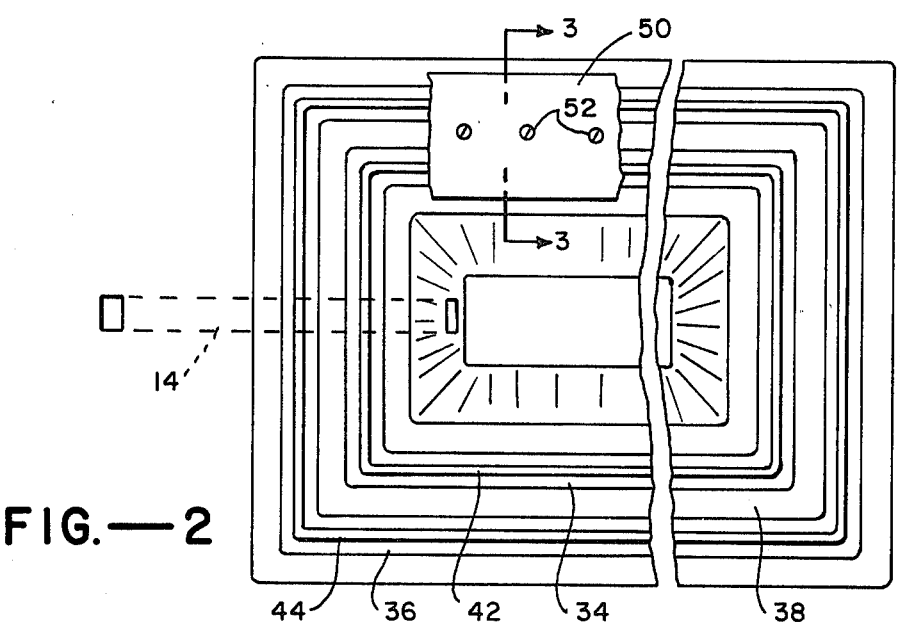
FIG.—2
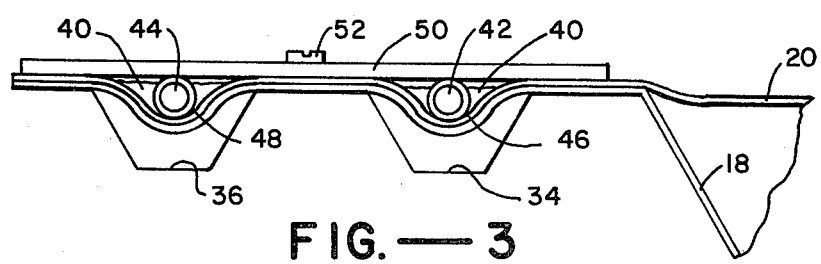
FIG.—3
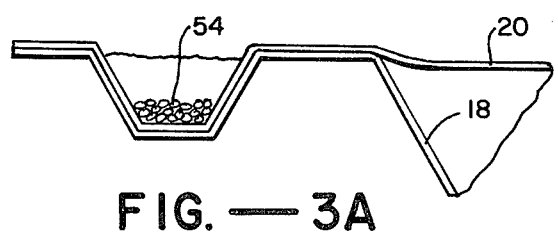
FIG.—3A

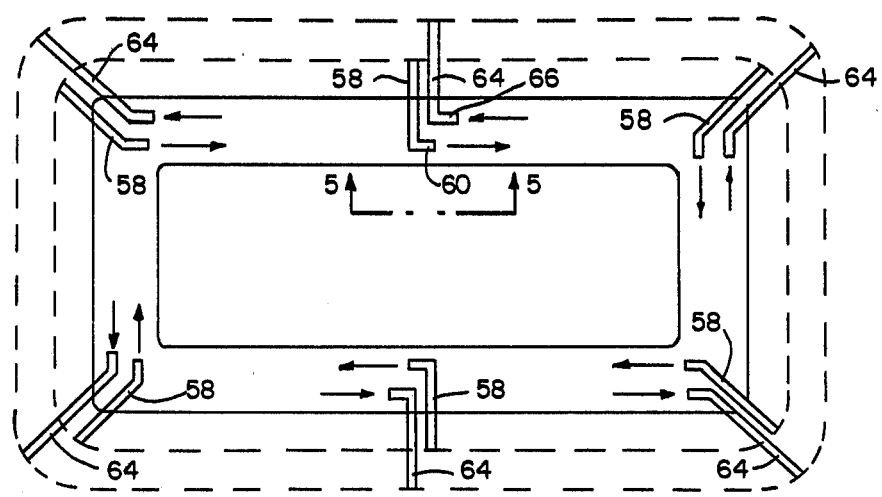
FIG.—4
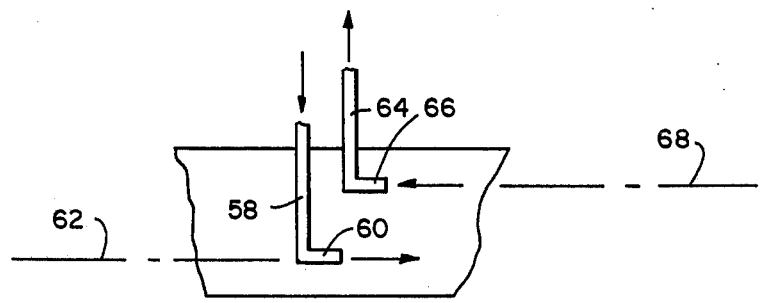
FIG.—5
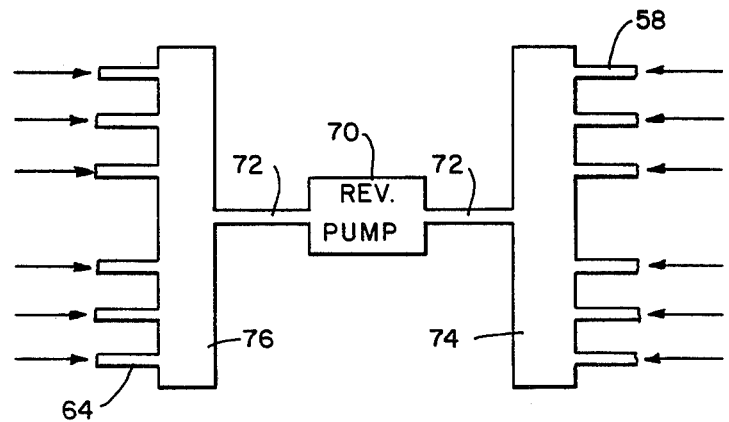
FIG.—6

SYSTEM FOR RECOVERING METHANE GAS FROM LIQUID WASTE

The present invention relates generally to techniques for recovering methane gas from liquid waste and more particularly to specific aspects of this technique.

The production of methane gas from liquid waste material by means of anaerobic fermentation is known in the art. The liquid waste which is actually a slurry of water and solid waste material is stored within a pit which is covered in an air tight fashion. In order to enhance fermentation of the waste and maximize the production of methane gas, the slurry should be maintained at a temperature of above 95° F.±5° and at a pH level of between about 7.4 and 7.8. The slurry itself should have a solids concentration of between about 85% and 92%.

The process just described is generally satisfactory for its intended purpose, that is, to produce methane gas. At the same time, the waste is stored odorlessly, and the nutrients within the waste can be retained for use as fertilizer. On the other hand, applicant has found aspects of this process which can be improved upon and which have been improved upon in accordance with the present invention, as will be discussed generally below and more specifically thereafter.

Accordingly, it is a general object of the present invention to improve upon the process described above in several different ways.

A more particular object of the present invention is to provide an uncomplicated, reliable and yet economical way of covering the storage pit recited above in an air sealed fashion.

Another particular object of the present invention is to provide a cover for the storage pit and means for seal connecting the cover around the pit in a way which allows the pit to be opened and closed in a relatively rapid fashion without causing damage to the cover itself.

Still another particular object of the present invention is to further increase the production of methane gas from the waste within the pit by agitating the waste during storage therein.

Yet another particular object of the present invention is to provide a specific method of agitating the stored waste.

Like the methane gas recovery technique described above, the technique disclosed herein utilizes an open pit extending into the ground, lined with a plastic sheet, concrete or other means and a cover sheet disposed over the pit. The technique disclosed herein also includes means for directing slurry into the pit so as to produce the methane gas therein, means for removing the produced gas and means for subsequently removing the waste from the pit.

In accordance with one aspect of the present invention, the technique disclosed herein utilizes means for disengagably holding a circumferential portion of the cover sheet adjacent to a section of the ground circumscribing the pit in an air sealed fashion, in a way which allows the sheet to be repeatedly used to cover and uncover the pit without damage thereto. This is to be contrasted with prior art techniques in which cover sheets are more permanently sealed into place. A second aspect of the present invention resides in the utilization of means for and the step of agitating the liquid waste within the pit whereby to increase its methane gas yield over what it would otherwise be without agitation. Both of these aspects of the present invention will be described in more detail hereinafter in conjunction with the drawings wherein:

FIG. 1 diagrammatically illustrates a system for recovering methane gas from liquid waste and specifically shows in vertical section a sealed pit utilized in this technique;

FIG. 2 is a partially broken away, top plan view of the sealed pit shown in FIG. 1;

FIG. 3 is a sectional view illustrating an aspect of the pit shown in FIGS. 1 and 2, taken generally along line 3—3 in FIG. 2;

FIG. 3A is a view similar to FIG. 3 but showing a modification of the particular aspect illustrated in FIG. 3;

FIG. 4 is a top plan view of the pit illustrated in FIG. 2 but in an unsealed, empty condition;

FIG. 5 is a side elevational view of a portion of the pit illustrated in FIG. 4, taken generally along line 5—5 in FIG. 4, illustrating the top and bottom agitational arrangement for reversible intake and outlet pipes; and FIG. 6 diagrammatically illustrates an operational aspect of the digester agitation system illustrated in FIG. 1 and particularly means for carrying out this operational aspect.

Turning now to the drawings, wherein like components are designated by like reference numerals throughout the various figures, attention is first directed to FIG. 1 which, as stated previously, diagrammatically illustrates a system for recovering methane gas from solid waste slurry, that is, a mixture of solid waste and water, hereinafter also referred to as liquid waste. This system is generally indicated by the reference numeral 10 and includes a relatively large open pit 12, for example on the order of 30,000 cubic feet in volume. A gravity feed pipe 14 or other suitable means is provided for directing successive batches of the solid waste slurry into pit 12 so as to ultimately ferment and produce methane gas. While not shown, suitable means may be provided for removing the waste from the pit after it has fermented and produced the maximum or desired amount of methane gas or the used waste could be removed manually. In FIG. 1, pit 12 is shown filled with a batch 16 of solid waste slurry. This waste material is in an aqueous slurry which is preferably between 8% and 15% solids. Moreover, while not shown, suitable heating means are preferably provided for maintaining batch 16 at a temperature between about 90° F. and 100° F. Also, each batch entering pit 12 can be provided with suitable chemicals sufficient to place the batch at a pH of between about 7.4 and 7.8.

The surface of pit 12 is preferably lined by suitable means, for example a liner 18 which is shown in FIG. 1 and which may be constructed with any suitable material such as PVC, synthetic rubber or fluorocarbon sheet or concrete. In addition, the pit is sufficiently sealed to promote anaerobic fermentation by means of a cover sheet or membrane 20 which extends over the entire top end of the pit and which is sealed around the latter in the manner to be described hereinafter. For the moment, it suffices to say that as the batch 16 of waste material is contained within the sealed pit 12 at the temperature and pH recited above, it produces methane gas as a result of anaerobic fermentation. This gas fills the space between the top surface of the batch and the underside of membrane 20. A suitable tubular arrangement generally indicated at 22 is provided for recovering this gas and directing it through an appropriate purification filter 24 to a suitable storage tank 26. The methane gas stored in tank 28 is used to drive a motor 28 through a suitable methane carburetor (not shown) and the motor is used to drive a generator 30 for producing electricity, thus completing an energy conversion process.

The overall system 10 for recovering methane gas in order to produce electricity as described thus far is known in the art and therefore has not been described in detail. However, the particular and preferred ways in which cover 20 may be sealed around pit 12 will be described in detail hereinafter along with a particular technique for agitating the slurry within the pit since these aspects of the overall system are provided in accordance with the present invention.

Referring to FIGS. 2 and 3 in conjunction with FIG. 1, attention is now directed to one specific technique for sealing down cover 20 in accordance with the present invention. As seen in FIGS. 1-3, two downwardly extending and upwardly opening concentric trenches, and inner trench or concrete trough 34 and an outer trench or concrete trough 36, are filled with water 40 and extend entirely around pit 12 along a section 38 of ground circumscribing the pit. Continuous hollow tubes 42 and 44 corresponding in configuration to the inner and outer trenches or concrete troughs 34 and 36, respectively, are disposed within these trenches. Each of these tubes is sufficiently closed so as to float within its respective trench which is filled with water or other type of liquid.

As best illustrated in FIG. 3 in conjunction with FIG. 2, concentric outer circumferential sections 46 and 48 of cover 20 are respectively disposed within trenches or concrete troughs 34 and 36 under tubes 42 and 44 and some of the water. Each circumferential tube is maintained at least partially submerged within its water filled trench by suitable means. As shown in FIG. 3, this is accomplished by means of a circumferential flat plate 50 extending entirely around the top of and covering both trenches or concrete troughs 34 and 36. The flat plate is held in place by readily removable screws or other such fastening devices 52 extending through corresponding sections of cover 20 and into the ground or concrete (or a cooperating threaded opening) between the two trenches. The flat plate is positioned relative to the trenches or concrete troughs so as to maintain each of the tubes in a partially submerged position. This maintains sections 46 and 48 of the cover submerged in the water filled trenches or concrete troughs which, in turn, results in two concentric air tight seals around pit 12 between cover 20 and the ground. At the same time, cover 20 can be readily removed without damage thereto merely by removing the screws or other such fastening devices 52 and pulling the cover out from under the tubes 46 and 48. By the same token, the cover can be readily placed in its sealed condition shown by reversing this procedure. Moreover, the same type of seal can be provided between outer circumferential sections of liner 18 and the ground surrounding pit 12 in the manner shown.

There are a number of ways in which the sealing approach described above could be modified. For example, the continuous tubes 42 and 44 could be replaced with discontinuous straight tubes closed at their opposite ends so as to be floatable and placed in end-to-end relationship with one another. There would be a sufficient number of tubes to extend the entire circumference of each trench. This latter approach would be preferable to providing "customized" continuous circumferential tubes since the latter would be more expensive to provide. On the other hand, the tubes themselves could be entirely replaced with gravel or similar weighted objects 54 illustrated in FIG. 3A. In this case, flat plate 50 and associated fastening devices 52 would not be necessary. However, it would be more difficult and time consuming to provide and remove the gravel than it would to fasten and unfasten flat plate 50 in order to seal and unseal cover 20.

As stated previously, another aspect of the present invention resides in the step of agitating the liquid waste 16 as it undergoes anaerobic fermentation in pit 12. This is accomplished by means of an arrangement best illustrated in FIGS. 4-6. As best seen in FIG. 4, the arrangement includes six outlet nozzles 58 (or more) positioned within and around the periphery of pit 12 at approximately equally circumferentially spaced points. These outlet nozzles include associated directional heads 60 disposed in a common plane 62 (indicated by dotted lines in FIG. 5). Each head faces in the same direction relative to the other heads, for example clockwise as shown in FIG. 4. Arrangement 56 also includes an equal number of inlet nozzles 64 which have directional heads 66 and which are respectively disposed in close proximity to outlet nozzles 58, as best seen in FIG. 4. The directional heads 66 are disposed within a common plane 68 (also indicated by dotted lines in FIG. 5) above previously recited plane 62.

Referring to FIG. 6, the arrangement is also shown including a reversible pump 70 and associated plumbing indicated generally at 72 for interconnecting an outlet manifold 74 and an inlet manifold 76. The outlet manifold is in fluid communication with all of the outlet nozzles 58 and the inlet manifold is in fluid communication with all of the inlet nozzles 64. Pump 70 serves to circulate the slurry in pit 12 along a closed path from the pit to and through the inlet nozzles and thereafter into inlet manifold 76. From this latter manifold, the liquid waste passes into outlet manifold 74 and thereafter through the outlet nozzles and back into the pit. During this procedure, there is constant movement in one direction by an upper layer of the slurry within the pit while there is constant movement in the opposite direction by a vertically lower layer, as indicated by the arrows illustrated in FIGS. 4 and 5.

While the solid waste slurry within pit 12 is preferably agitated in the manner described utilizing arrangement 56, it is to be understood that other means of agitation could be utilized. In any event, it has been found that intermittent agitation during the anaerobic fermentation of the waste increases the amount of methane which is generated by a given amount of waste material, everything else being equal.

What is claimed is:

1. A system for recovering methane gas from liquid waste, comprising: an open pit extending into the ground; a cover sheet disposed over said pit; means for disengagably holding a circumferential portion of said cover sheet adjacent to a section of the ground circumscribing said pit in an air sealed fashion, whereby said sheet can be repeatedly used to cover and uncover said pit without damage to the sheet, said holding means including a downwardly extending and upwardly opening trench which extends around said pit along said section of ground circumscribing the latter and which is filled with water for receiving said circumferential portion of said cover, said holding means also including means located within said trench for maintaining a circumferential segment of said sheet portion under the water in said trench; means for directing liquid waste into said pit so as to produce said methane gas within said pit; means for removing said gas from said pit; and means for removing the waste from said pit.

2. A system according to claim 1 wherein said last-mentioned means includes rock material located within said trench and over said circumferential sheet segment for maintaining said segment under the water in the trench.

3. A system according to claim 1 wherein said last-mentioned means includes water floatable tubular means located within and along substantially the entire length of said trench over said circumferential sheet segment and means for maintaining said tubular means at least partially submerged within the water in said trench.

4. A system according to claim 3 wherein said tubular means includes a plurality of hollow tubes closed at their ends and placed in end-to-end relationship to one another in said trench.

5. A system according to claim 3 wherein said tubular means includes a single circumferential hollow tube configured to fit within said trench.

6. A system according to claim 1 including means for agitating the waste within said pit.

7. A system according to claim 6 wherein said agitating means includes means for causing a first horizontal layer of waste within said pit to circulate circumferentially around the pit in one direction and for causing a second lower horizontal layer of said waste to circulate circumferentially around the pit in the opposite direction.

8. A system according to claim 1 including a liner sheet extending over and lining the surface of said pit, said liner sheet including an outer circumferential portion extending outside said pit adjacent said circumferential portion of said cover sheet, said means for disengagably holding said circumferential portion of said cover sheet adjacent to a section of the ground circumscribing said pit in an air sealed fashion also disengagably holding the circumferential portion of said liner sheet adjacent to said ground section in an air sealed fashion.

9. A system for recovering methane gas from liquid waste, comprising: an open pit extending into the ground; a pair of downwardly extending and upwardly opening trenches circumscribing said pit along a section of the ground adjacent to the uppermost periphery of the pit, said trenches being filled with water; a liner sheet extending over the surface of said pit for lining the latter, said liner sheet including outer concentric circumferential portions disposed within said trenches; a cover sheet disposed over said pit and liner sheet, said cover sheet including concentric outer circumferential portions disposed within said trenches; water floatable tubular means located within and along substantially the entire extent of each of said trenches over the circumferential liner and cover sheet portions therein; means for maintaining the tubular means in each trench at least partially submerged within the water therein whereby to hold said circumferential portions in place within the water in each trench; means for directing liquid waste into said pit above said liner sheet and below said cover sheet so as to produce methane gas within the pit; and means for removing said gas from said pit; and means for removing the waste from said pit.

* * * * *